(12) United States Patent
Koroteev et al.

(10) Patent No.: US 9,558,588 B2
(45) Date of Patent: Jan. 31, 2017

(54) METHOD FOR BUILDING A 3D MODEL OF A ROCK SAMPLE

(75) Inventors: Dmitry Anatolievich Koroteev, Moscow (RU); Alexander Nikolaevich Nadeev, Spring, TX (US); Ivan Viktorovich Yakimchuk, Moscow (RU); Igor Andreevich Varfolomeev, Moscow (RU)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 14/411,415

(22) PCT Filed: Jun. 26, 2012

(86) PCT No.: PCT/RU2012/000508
§ 371 (c)(1),
(2), (4) Date: May 18, 2015

(87) PCT Pub. No.: WO2014/003596
PCT Pub. Date: Jan. 3, 2014

(65) Prior Publication Data
US 2015/0262417 A1    Sep. 17, 2015

(51) Int. Cl.
*G06K 9/00* (2006.01)
*G06T 17/05* (2011.01)
(Continued)

(52) U.S. Cl.
CPC .............. *G06T 17/05* (2013.01); *G01N 23/046* (2013.01); *G01N 33/24* (2013.01); *G06T 5/002* (2013.01);
(Continued)

(58) Field of Classification Search
CPC ............ G01N 2223/419; G01N 23/046; G01N 2223/616; G01N 2223/649; G01N 33/24; G01N 15/088; G01N 2015/0846; G06T 2207/10081; G06T 7/0004; G06T 17/05; G06T 7/0081; G06T 2207/10116; G06T 2207/20032; G06T 2207/30184; G06T 5/20;  G06T 7/00
See application file for complete search history.

(56) References Cited

U.S. PATENT DOCUMENTS

| 5,469,488 A | 11/1995 | Ono |
| 6,345,112 B1 | 2/2002 | Summers et al. |

(Continued)

FOREIGN PATENT DOCUMENTS

| RU | 2436161 C2 | 12/2011 |
| WO | 2009140738 A1 | 11/2009 |

(Continued)

OTHER PUBLICATIONS

Sezgin, et al., "Survey over image thresholding techniques and quantitative performance evaluation", Jan. 2004, Journal of Electronic Imaging, vol. 13, No. 1, pp. 146-165.
(Continued)

*Primary Examiner* — Tom Y Lu

(57) ABSTRACT

A method for building a 3D model of a rock sample comprises performing X-ray micro/nanoCT scanning of a rock sample and obtaining its initial three-dimensional microstructure image in a gray scale. Then, an analysis of the obtained three-dimensional image of the rock sample is performed and a binarization method is selected in dependence of the image quality and properties of the rock sample. The selected binarization method is at least once applied to the obtained initial three-dimensional image of the sample. Obtained 3D binarized image represents a 3D model of the rock sample.

16 Claims, 4 Drawing Sheets

(51) Int. Cl.
 G01N 33/24 (2006.01)
 G01N 23/04 (2006.01)
 G06T 5/20 (2006.01)
 G06T 7/00 (2006.01)
 G06T 5/00 (2006.01)
 G06T 5/40 (2006.01)

(52) U.S. Cl.
 CPC . *G06T 5/20* (2013.01); *G06T 5/40* (2013.01); *G06T 7/00* (2013.01); *G06T 7/0081* (2013.01); *G01N 2223/419* (2013.01); *G01N 2223/616* (2013.01); *G01N 2223/649* (2013.01); *G06T 2207/10081* (2013.01); *G06T 2207/10116* (2013.01); *G06T 2207/20032* (2013.01); *G06T 2207/20192* (2013.01); *G06T 2207/30184* (2013.01)

(56) References Cited

U.S. PATENT DOCUMENTS

| | | | | |
|---|---|---|---|---|
| 8,081,796 B2* | 12/2011 | Derzhi | .................. | E21B 49/005 378/53 |
| 8,331,626 B2* | 12/2012 | Wojcik | .................. | G01N 23/046 382/109 |
| 2011/0004447 A1* | 1/2011 | Hurley | .................... | G06T 17/00 703/1 |
| 2014/0044315 A1* | 2/2014 | Derzhi | .............. | G06K 9/00624 382/109 |

FOREIGN PATENT DOCUMENTS

| | | |
|---|---|---|
| WO | 2011002765 A2 | 1/2011 |
| WO | 2011062807 A1 | 5/2011 |

OTHER PUBLICATIONS

Wirjadi, "Survey of 3D Image Segmentation Methods", 2007, Berichte des Fraunhofer ITWM, No. 123, 29 pages.

Knackstedt, et al., "Digital Core Laboratory: Properties of Reservoir Core Derived from 3D Images", Mar. 29-30, 2004, SPE Asia Pacific Conference on Integrated Modelling for Asset Management in Kuala Lumpur, Malaysia, SPE Paper 87009, 14 pages.

International Search Report & Written Opinion issued in related PCT application No. PCT/RU2012/000508 on Mar. 28, 2013, 6 pages.

Young, et al., "Fundamentals of Image Processing", 1995, Delft University of Technology, ISBN 90-75691-01-7, NUGI 841, pp. 54-61.

* cited by examiner

000

METHOD FOR BUILDING A 3D MODEL OF A ROCK SAMPLE

FIELD OF THE INVENTION

The invention relates to X-ray based analysis of a rock sample, namely microtomography (microCT) and nanotomography (nanoCT) techniques.

BACKGROUND OF THE INVENTION

X-ray micro- and nano-computed tomography is a well-known non-destructive technique for visualizing and quantifying the internal structure of objects in three dimensions (3D). It is used to provide high resolution images of rocks in 2D or 3D at a micron scale (see, for example, M. A. Knackstedt et al., "Digital Core Laboratory: Properties of Reservoir Core Derived From 3D Images," SPE 87009, 2004).

X-ray micro- and nano-computed tomography techniques enable acquisition of grayscale 3D images in which the grayscale represents the X-ray absorption distribution within the object. The absorption (attenuation) depends on the chemical composition of the material and its physical density. The range of X-ray energies used in computed tomography (CT) allows the study of very dense objects, such as rocks.

Strong contrast in X-ray attenuation coefficients between rock grains and air/water/oil-filled pores, the allows the microCT technique reproducing 3D images with dark and bright areas inside. The dark and bright areas correspond to pores and grains respectively (if, as usual, the 3D microCT image is considered at inverse gray scale). The problem is that the boundary between dark and bright regions is not step-like. In order to segment a rather smoothed grayscale microCT image in two phases (grains and pores) it is necessary to apply binarization operation which can be revealed in many different ways. For example, a number of approaches to binarization are described in [M. Sezgin, B. Sankur, "Survey over image thresholding techniques and quantitative performance evaluation", Journal of Electronic Imaging 13(1), 146-165 (January 2004)].

It is known a patent application WO2009140738 A1 titled "Image data processing" and aimed at creating a rock model based on different imaging techniques for extracting an information about sample. Main disadvantage of this application is presence of 2D-3D image registration as necessary step for building the 3D digital model accounting pore space and mineral distribution.

Another disadvantage is necessity of making thin sections as sources for 2D mineral maps from SEM or optical microscopy. It is known that making this sections is destructive at microscale. This makes their 2D-3D registration procedure nearly non-applicable in real life. Furthermore, preparing thin sections from the sample after X-Ray microCT destructs original sample, so no further investigations with original sample are possible.

Suggested method provides digital representation of rock's internal structure. Besides, it does not include 2D-3D registration for 3D building the 3D model of the core.

SUMMARY OF THE INVENTION

A method for building a 3D model of a rock sample comprises performing X-ray micro/nanoCT scanning of a rock sample and obtaining its initial three-dimensional microstructure image in a gray scale. Then, an analysis of the obtained three-dimensional image of the rock sample is performed and a binarization (multicomponent segmentation) method is selected in dependence of the image quality and properties of the sample. The selected binarization method is at least once applied to the obtained initial three-dimensional image of the sample. Obtained 3D binarized image represents a 3D model of the rock sample.

Selecting a binarization method includes selecting a global binarization thresholding method when porosity of the rock sample is known, pores of the rock sample have sizes above the resolution and the initial three-dimensional microstructure image does not contain significant artifacts.

Selecting a binarization method includes selecting an automated or a local binarization thresholding method when porosity of the rock sample is unknown, or pores of the sample have sizes under the resolution, or the initial three-dimensional microstructure image contains significant artifacts.

DETAILED DESCRIPTION OF THE INVENTION

Figure 4:
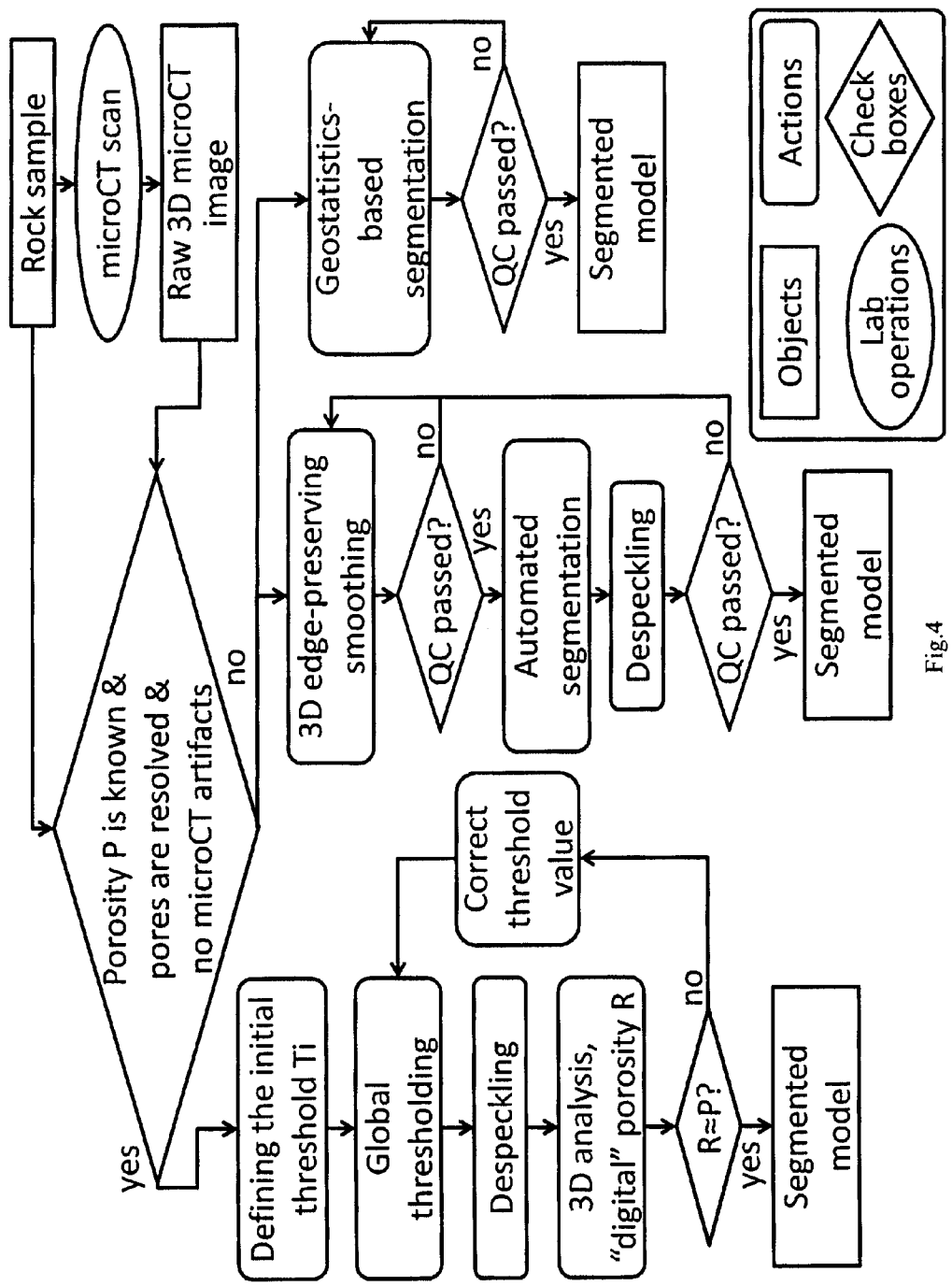
FIG. 4 is a detailed flowchart illustrating an exemplary 3D model building method.

Detailed flowchart illustrating an exemplary 3D model building method is shown on FIG. 4. In the present example, rock samples (core plugs, drilling cuttings, other rocks) are transported to a computer tomographic ("CT") scanner, which may use x-rays for analysis of internal structure of the samples and for generation of three dimensional (3D) images of the samples. An X-ray micro/nanoCT scanning of a rock sample is performed at a particular resolution and a 3D initial image in gray scale is obtained.

Then analysis of the obtained initial three-dimensional image of the rock sample is performed, namely the presence of significant artifacts (microCT ring artifacts, smoothing due to thermal drifts of an X-ray source, beam hardening artifact, partial volume effects, signal-to-noise levels) is checked. A binarization method is selected in dependence of the image quality and properties of the rock sample. Image binarization refers to the process of converting an image represented by pixel values which may assume multiple levels to pixel values which can be one of two values, e.g., a first value corresponding to foreground and a second value corresponding to background. Image binarization can be used convert a gray scale or a color image to a black and white image.

If the sample has pores with sizes above the resolution, porosity P of the rock sample is known from different measurements and the obtained initial 3D image does not contain significant artifacts, a global binarization thresholding method is selected and applied to the obtained initial three-dimensional image of the sample. An initial threshold value Ti for all the pixel intensities of the image is defined to split pores and solid skeleton. Voxels with grayscale values lower than Ti are to be marked as black (pores), others as white (solid grains).

Figure 1:
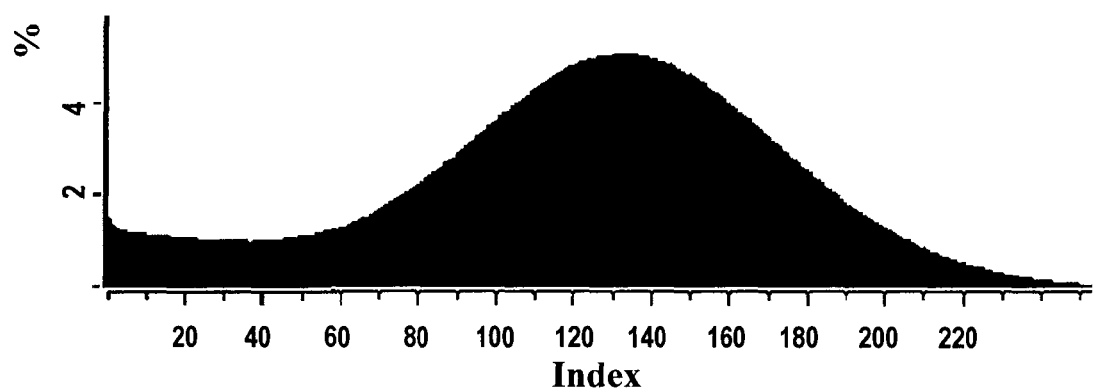
FIG. 1 illustrates a typical grayscale histogram of 8 bit 3D microCT image of a geological sample.

Usually a histogram of 3D microCT image does not look like a function with two well-shaped peaks. Most frequently it contains one smoothed peak and two relatively high columns at minimal and maximal values of a grayscale range (0 and 255 for 8-bit images). Typical form of the histogram is presented in FIG. 1. For such type histograms it is recommend to chose Ti in neighborhood of a grayscale level g at which second derivative of histogram h" (g) stops fluctuating around zero value and becomes sufficiently positive (see FIG. 1, where Ti is chosen to be 59). In simple words the initial threshold should be chosen at the point where histogram function starts increasing in non-linear manner (with exponent higher than one). In some cases the histogram represents two-peak structure, where left peak stands for pores, and right one stands for solid skeleton. In this case the Ti might be chosen at local minima between the peaks.

Despeckling operations can be applied to remove parasitic internal pores and solid objects surrounded by porous space.

The porosity R of the 3D sample can be calculated (by dividing volume of segmented pores by total volume of the sample) and then the known porosity P of the rock sample is compared with the calculated porosity R. When the calculated porosity differs from known porosity the initial general threshold value is changed and the selected global binarization thresholding method is applied repeatedly until the calculated porosity will be equal to known porosity.

Thus, if R≈P, the obtained 3D binary image is saved and can be used as a model for flow simulations inside. If R<P, the selected global binarization thresholding method is applied with threshold values Ti+1, Ti+2 . . . until R≈P. If R>P, the selected global binarization thresholding method is applied with threshold values Ti−1, Ti−2 . . . until R≈P.

According to one embodiment of the invention, when porosity of the rock sample is unknown, or pores of the sample have sizes under the resolution, or the initial three-dimensional microstructure image contains significant artifacts an automated binarization thresholding method can be selected.

At first a 3D edge preserving smoothing of the obtained initial three-dimensional image of the rock sample is performed by any of known 3D edge-preserving noise-reducing algorithms. 3D edge preserving smoothing might be performed by one of known image filters: anisotropic diffusion filter, Kuwahara filter, non-linear diffusion filter, median filter, mean shift filter, or any other 3D edge-reserving noise-reducing algorithms (http://tnw.tudelfi.nl/fileadmin/Faculteit/TNW/Over_de_faculteit/Afdelingen/Imaging_Science_and Technology/Research/Research Groups/Quantitative_Imaging/Publications/List_Publications/doc/FIP2.2.pdf).

A quality of performed 3D edge preserving smoothing of the obtained initial three-dimensional image of the rock sample is checked and when the quality is not good (i.e. noise is not reduced up to the level appropriate for appearing separate peaks at histogram, and/or of grains edges are shifted at filtering) at least one additional 3D edge preserving smoothing of the obtained initial three-dimensional image of the sample is performed by another 3D edge-preserving noise-reducing algorithm. The quality might be checked by analyzing the difference between initial and smoothed images, which allows making sure that edges are conserved.

Then the selected automated thresholding method is applied by using features of the histogram of filtered image. The automated thresholding might be performed by using one of the following algorithms: thresholding at local minima between main histogram peaks; Otsu-type thresholding; Entropy-based thresholding or other methods for automated binarization (http://web.cs.wpi.edu/~trascrizione/MethSurvey.pdf).

Figure 2A:
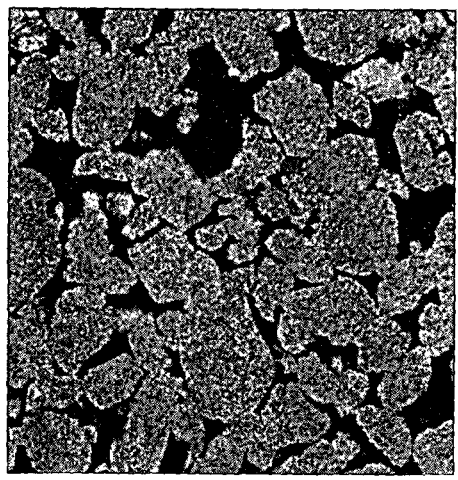
FIG. 2 shows a piece of a 2D cross-section of an initial 3D image (2a) and result of application of a global binarization thresholding method (2b).
Figure 2B:
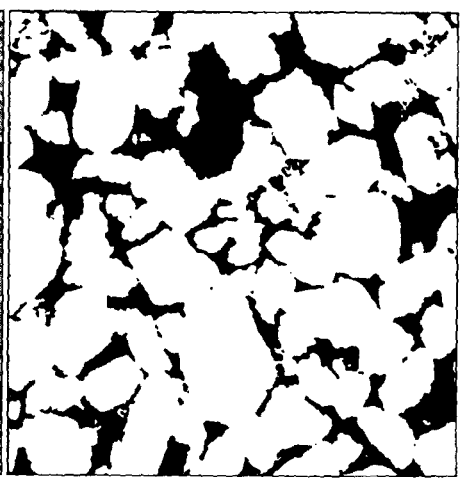

FIG. 2 shows a piece of a 2D cross-section of an initial 3D image (2a) and result of application of a global binarization thresholding method (2b).

Despeckling operations can be applied to remove parasitic internal pores and solid objects surrounded by porous space.

Then a quality of the binarized image is checked. If the quality is not good (edges are moved from where they are at initial microCT image) at least once another known method for automated binarization is applied to the obtained initial three-dimensional image of the sample. The quality might be checked by analyzing the positions of edges at initial and binarized images.

According to another embodiment of the invention, when porosity of the rock sample is unknown, or pores of the sample have sizes under the resolution, or the initial three-dimensional microstructure image contains significant artifacts a local binarization thresholding method can be selected. The Kriging or indicator Kriging procedure might be chosen here for example [http://www.google.com/url?sa=t&rct=j&q=indicator%20kriging%20segmentation&source=web&cd=7&ved=0CFMQFjAG&url=http%3A%2F%2Fkluedo .ub.uni-kl.de%2Ffiles%2F1978%2 Fbericht123. pdf&ei=tUF9T7jtArLP4QSV9eD1DA&usg=AFQjCNHy5 flvqaueeQ6m41F7c_xNsDSJjg]

Figure 3A:
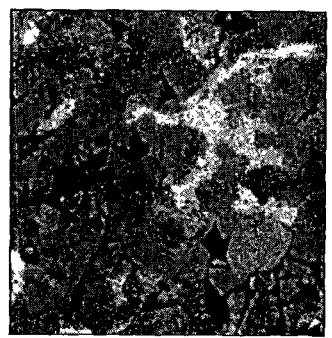
FIG. 3 demonstrates an example of application of an automated binarization thresholding method. 3a is a 2D cross section of an initial 3D image, 3b is filtered data, and 3c is a binarized image.
Figure 3B:
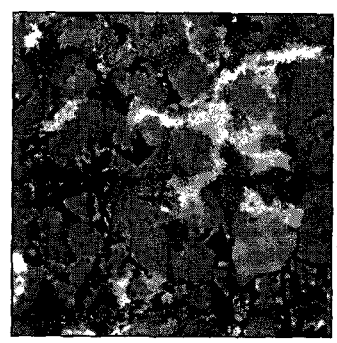
Figure 3C:
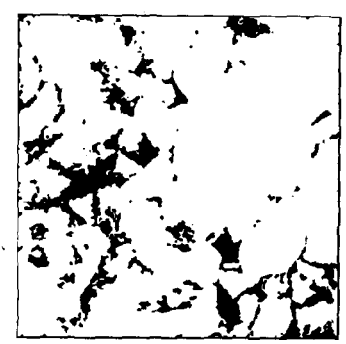

A quality of the obtained binarized model can be checked and if the quality is not good ((edges are moved from where they are at initial microCT image)) at least once the local binarization thresholding method with another binarization parameters (sets of binarization parameters for each individual thresholding approach is different, see examples at http://web.cs.wpi.edu/~trascrizione/MethSurvey.pdf) is applied to the obtained initial three-dimensional image of the sample. The quality might be checked by analyzing the positions of edges at initial and binarized images. On FIG. 3 it is shown an example of application of an automated binarization thresholding method. 3a is a 2D cross section of an initial 3D image, 3b is filtered data, and 3c is a binarized image.

The invention claimed is:

1. A method for building a 3D model of a rock sample, the method comprising:
performing X-ray micro/nanoCT scanning of a rock sample at a particular resolution,
obtaining an initial three-dimensional microstructure image of the rock sample in a gray scale,
performing analysis of the obtained initial three-dimensional microstructure image of the rock sample, the analysis includes checking the presence of significant artifacts,
selecting a global binarization thresholding method if a porosity of the rock sample is known, pores of the rock sample have sizes above the resolution and the initial three-dimensional microstructure image does not contain significant artifacts,
selecting an automated binarization thresholding method if the pores of the rock sample have sizes under the resolution or the initial three-dimensional microstructure image contains significant artifacts,
selecting an automated binarization thresholding method or a local binarization thresholding method if the porosity of the rock sample is unknown, at least once applying the selected binarization method to the obtained initial three-dimensional microstructure image of the rock sample, obtaining a 3D binarized image representing a 3D model of the rock sample.

2. The method of claim 1 wherein selecting the global binarization thresholding method includes using an initial general threshold value.

3. The method of claim 2 wherein said initial general threshold value is chosen at the point on a histogram where a histogram function starts increasing in non-linear manner.

4. The method of claim 2 wherein said initial general threshold value is chosen at local minima between peaks on a histogram.

5. The method of claim 1 further comprising applying despeckling operations to the obtained 3D binarized image to remove parasitic internal pores and solid objects surrounded by a porous space.

6. The method of claim 2 further comprising calculating porosity of the rock sample and comparing the known porosity of the sample with the calculated porosity; and when the calculated porosity differs from known porosity changing the initial general threshold value and applying the selected global binarization thresholding method repeatedly until the calculated porosity will be equal to the known porosity.

7. The method of claim 1 wherein the selected automated binarization thresholding method is a known method for automated binarization.

8. The method of claim 7 wherein the known method for automated binarization is selected from a group consisting of: thresholding at local minima between main peaks on a histogram, Otsu-type thresholding, entropy-based thresholding.

9. The method of claim 1 wherein the selected automated binarization thresholding method includes preliminary applying a 3D edge preserving smoothing of the obtained initial three-dimensional microstructure image of the sample performed by any of known 3D edge-preserving noise-reducing algorithms.

10. The method of claim 9 wherein said 3D edge preserving smoothing of the obtained initial three-dimensional microstructure image of the sample is performed by one of image smoothing filters selected from a group consisting of: an anisotropic diffusion filter, a Kuwahara filter, a non-linear diffusion filter, a median filter, a mean shift filter.

11. The method of claim 9 further comprising checking a quality of performed 3D edge preserving smoothing of the obtained initial three-dimensional image of the sample and if necessary performing at least one additional 3D edge preserving smoothing of the obtained initial three-dimensional image of the sample performed by another 3D edge-preserving noise-reducing algorithm.

12. The method of claim 7 further comprising checking a quality of the obtained binarized image and if necessary at least once applying another known method for automated binarization to the obtained initial three-dimensional image of the sample.

13. The method of claim 12 wherein the quality of the obtained binarized image is checked by analyzing positions of edges at the obtained initial three-dimensional image of the sample and at the binarized image.

14. The method of claim 1 wherein the selected local binarization thresholding method is Kriging or indicator Kriging procedure.

15. The method of claim 1 further comprising checking a quality of the binarized image obtained using the local binarization thresholding method, and if necessary at least once applying the local binarization thresholding method with other binarization parameters to the obtained initial three-dimensional microstructure image of the sample.

16. The method of claim 15 wherein the quality of the obtained 3D binarized image is checked by analyzing positions of edges at the obtained initial three-dimensional microstructure image of the sample and at the binarized image.

* * * * *